US005700451A

United States Patent [19]

Yue et al.

[11] Patent Number: 5,700,451
[45] Date of Patent: Dec. 23, 1997

[54] SUNSCREEN COMPOSITION

[75] Inventors: Jiang Yue; Lisa Renee Dew, both of West Chester; Donald Lynn Bissett, Hamilton, all of Ohio

[73] Assignee: The Procter & Gamble Company, Cincinnati, Ohio

[21] Appl. No.: 448,942

[22] Filed: May 24, 1995

[51] Int. Cl.$^6$ .............................. A61K 7/42; C01G 23/047
[52] U.S. Cl. .............................. 424/59; 423/610; 428/402; 514/772
[58] Field of Search .............................. 423/610; 424/59; 428/402; 514/772

[56] References Cited

U.S. PATENT DOCUMENTS

| | | | |
|---|---|---|---|
| 4,820,508 | 4/1989 | Wortzman | 424/59 |
| 5,024,827 | 6/1991 | Jones et al. | 423/610 |

FOREIGN PATENT DOCUMENTS

| | | | |
|---|---|---|---|
| 0526712A1 | 10/1993 | European Pat. Off. | A61K 7/42 |
| 57-067681 | 4/1982 | Japan | C09K 3/00 |
| 62-207718 | 9/1987 | Japan | C01G 23/04 |
| 63-17221 | 1/1988 | Japan | C01G 23/053 |
| 4-367512 | 12/1992 | Japan | C01G 23/047 |
| 0-6227944A | 2/1993 | Japan | A61K 7/02 |
| 5-279235 | 5/1993 | Japan | A61K 7/42 |
| 684387 | 4/1993 | Switzerland | A61K 7/42 |
| WO 90/11067 | 10/1990 | WIPO | A61K 7/42 |
| WO94/18932 | 9/1994 | WIPO | A61K 7/00 |
| WO94/18940 | 9/1994 | WIPO | A61K 7/42 |

OTHER PUBLICATIONS

Brown et al., "Testing UVA and UVB Protection From Microfine Titanium Dioxide", *Cosmetics & Toiletries*, vol. 105, pp. 69–73, 1990.
Robb, et al., "Scattering & Absorption of UV Radiation by Sunscreens Containing Fine Particle & Pigmentary Titanium Dioxide", *DCI*, pp. 32–39, Mar., 1994.
Derwent: GB2276157-A, Sep. 21, 1994, Abstract.
Patent Abstracts of Japan, vol. 012, No. 398 (C–538), JP,A,63 141912, Abstract. Jun. 14, 1988.
Patent Abstracts of Japan, vol. 013, No. 011 (C–558), JP,A,63 218615, Abstract. Sep. 12, 1988.

*Primary Examiner*—Shelley A. Dodson
*Attorney, Agent, or Firm*—Loretta J. Henderson; Richard A. Hake; John M. Howell

[57] ABSTRACT

A $TiO_2$ hydrogel and method of preparation therefor is disclosed: $TiO_2$ particles ranging in size from at least about 50 nm to about 150 nm wherein the particle is about 20% to about 90% anatase are disclosed. Topical sunscreen compositions, which comprise 1% to about 15% anatase/amorphous $TiO_2$ are also disclosed. This composition provides UVA and UVB protection without concomitant dulling or discoloring the skin. The composition also has enhanced stability, is invisible, is easy to apply in an even manner and resists discoloration (or "color-changing") or decomposition on the shelf or on the skin.

12 Claims, No Drawings

SUNSCREEN COMPOSITION

FIELD OF THE INVENTION

This invention relates to topical compositions, preferably topical sunscreen compositions, comprising about 1% to about 15% anatase/amorphous $TiO_2$ which is about 20% to about 90% crystalline.

BACKGROUND

There are two basic types of ultraviolet absorbing actives used in sunscreens.

(1) Organic compounds which absorb ultraviolet light and convert it to thermal energy. Examples of such organic compounds include p-aminobenzoic acid derivatives, salicylic acid derivatives, azole derivatives, benzophenone derivatives, urocanic acid, quinine salts, etc. It is difficult to provide constant ultraviolet protection over a long period due to UV induced degradation and concomitant change in absorption characteristics. In addition, many of these ultraviolet absorbers have been criticized recently because they can be absorbed through the skin and may cause side effects.

(2) Inorganic compounds which have an energy gap (or "band gap") equivalent to the energy of the incident ultraviolet light. The ultraviolet light is absorbed and/or scattered. Examples of such inorganic materials include zinc oxide, clays, such as kaolin and the like. These are typically stable and non-toxic, and usually consist of particles which are large, thus scattering visible light in addition to their desired function of absorbing and/or scattering ultraviolet light. Thus, a topical composition used as a sunscreen, which contains such pigment particles, can be dull, colored or opaque, thus imparting a dull or discolored look to the skin. This is often considered by consumers an unacceptable drawback.

$TiO_2$ is light colored or white inorganic material. When used in cosmetics as a sunscreen, it has heretofore demonstrated the dulling and discoloring look associated with inorganic materials. $TiO_2$ can exist in different forms; including the crystalline forms rutile and anatase, and a non-crystalline form (i.e., amorphous).

The most common crystalline form of $TiO_2$ is rutile. Rutile $TiO_2$ is found in nature and can contain up to 10% iron. This form of $TiO_2$ is often used as a pigment and is known primarily for its high refractive index and "bluish" color. Because of its high refractive index, refined rutile $TiO_2$ is one of the primary white hiding pigments in paint and coatings. This high refractive index is useful in shielding the skin from ultraviolet radiation and visible light, but provides a "whitewashed" appearance when applied to the skin.

The use of rutile $TiO_2$ for sunscreens is described in Robb, et al "Scattering & Absorption of UV Radiation by Sunscreens Containing Fine Particle & Pigmentary Titanium Dioxide" *Drug and Cosmetic Industry*, pp. 32–39 (March 1994), which discloses UV absorption and light scattering by particles of rutile $TiO_2$ ranging in size from 20–220 nm.

The art has described other sunscreens containing $TiO_2$. For example, PCT published application WO 90/11067 (Boots) describes a sunscreen comprising $TiO_2$ in a blend of particle sizes (1–100 nm, preferably 15–50 nm), having as a primary particle size of about 15 nm and at least one particle size of between 30 and 50 nm. Commercially available rutile $TiO_2$ is exemplified and described. As a further example, Brown et al. "Testing UVA and UVB protection from Microfine Titanium Dioxide" *Cosmetics and Toiletries* Vol. 105, pp. 69–73 (December 1990), describes testing methods for $TiO_2$ sunscreens. Based on the physical data for an example using rutile $TiO_2$, the preferred particle size is said to be between 180 and 220 nm.

In each of the preceding references, rutile $TiO_2$ is characterized as giving an undesirable "bluish" or "whitening" effect to the skin. While it may work as a sunscreen, it is not favored for the same reasons colored pigments are not favored; they cause the skin to look natural. Hence the art, as well as the consumer, tends not to view rutile $TiO_2$ as an acceptable sunscreen agent.

The art recognizes that the anatase and rutile forms of $TiO_2$ are not equivalent in function. For example, anatase and rutile differ in physical properties, e.g., band gap, refractive index and color. More specifically, anatase has a distinctly yellowish tinge, hence it imparts a "sallow color" to the substrate (e.g., skin) on which it is applied. Anatase also has a lower refractive index and a higher energy band gap than rutile $TiO_2$.

EPO published application 526,712 (Shiseido) discloses a "photochromic cosmetic" (or color changing cosmetic). The cosmetic includes between 1% and 60% by weight of a "photochromic ultra-violet ray shield powder, which contains at least 50% anatase type titanium dioxide" which "responds to" light. The primary particle size is said to be about 15 nm, but is said to also be combined with particles from 30 nm to 50 nm. Rutile $TiO_2$ is included in the composition because of its shielding effect. One of the potential drawbacks of the particular anatase particles described in EPO 526,712 is its photoreactivity or changing color in the presence of light. Anatase particles exposed to sunlight have been known to react with other species in compositions. This instability can cause color changes or inactivation of the actives in compositions containing anatase.

JP-04-367512 discloses a method of preparing anatase titanium dioxide microparticles having a length-average diameter of 0.5–2.5 μm. Sho-63 (1988)-17221 (Taki kagaku) discloses a method of preparing crystalline anastase titanium oxide so that has a particle size of 500 Angstroms (i.e., 50 nm) or less. U.S. Pat. No. 5,024,827 (Jones) describes an acidic process for making small (10 nm to 250 nm) particles of $TiO_2$ having "at least 80% of the $TiO_2$ in anatase form." European Patent Application 526,712, assigned on its face to Shiseido, discloses a process for preparing $TiO_2$ having a surface area between $25 m^2/g$ and $100 m^2/g$. Surface area, rather than internal dimension (i.e. diameter), is described. Japanese Patent Application 04-367512 assigned to Naito Ceramics discloses a process for making spherical porous anatase $TiO_2$ with an average diameter from 500 to 2500 nm aggregated into porous spherical particles.

The art also acknowledges non-crystalline or "amorphous" $TiO_2$. This material, due to its lack of crystallinity, does not have a well defined refractive index, bandgap or the like. It is not widely used because it is not easily characterizable.

It would be very desirable and advantageous to provide a stable cosmetic composition that covers easily, effectively shields skin from ultraviolet light over a wide range of wavelengths (i.e. the UVA and UVB), maintains its ultraviolet absorbing capabilities over a long period of time (i.e., it is a "stable sunscreen"), and provides excellent visible range transparency (i.e., it is "invisible," or not readily noticeable on the skin), while avoiding the appearance of skin discoloration or dulling or changing of color upon exposure to light (i.e., photoreactivity, manifested, for example, by the coloring of the skin to make it appear unnatural upon application, wear or exposure to the sun and the like, e.g., the skin may appear "yellower" than normal or "bluer" than normal.). It is an object of the present invention to provide topical compositions having one or more of these desirable and advantageous properties.

SUMMARY OF THE INVENTION

The applicant has found that anatase/amorphous $TiO_2$, containing about 20% to about 90% anatase, provides UVA and UVB protection without concomitant dulling or discoloring the skin, and is particularly useful as a sunscreen. In one aspect, the invention relates to such anatase/amorphous $TiO_2$ in the form of a hydrogel of about 20% to about 60% solids (primarily anatase/amorphous $TiO_2$). In another aspect, the invention relates to such anatase/amorphous $TiO_2$ in the form of particles that are formed from the hydrogel and which range in size from at least about 50 nm to about 150 nm. The individual particles are about 20% to about 90% anatase. In another aspect, the invention relates to a method of preparation of the anatase/amorphous $TiO_2$ hydrogel and particles. In yet another aspect, the invention relates to a topical composition, useful as a sunscreen, comprising about 1% to about 15% anatase/amorphous $TiO_2$ containing about 20% to about 90% anatase in either the hydrogel form or particles formed therefrom.

DETAILED DESCRIPTION OF PREFERRED EMBODIMENTS

As used herein the term "hydrogel" refers to the colloidal precipitate formed from aqueous solutions of semihydrated $TiO_2$. The term "colloidal precipitate" as it relates to inorganic compounds is described in Cotton and Wilkinson, *Advanced Inorganic Chemistry* Wiley publishing (1987) and in C. J. Brinker; G. W Scherer *Sol-gel Science*, Academic Press, Inc. (1990). The hydrogel is prepared, for example, by reacting a titanium species with a reactive oxyanion containing species to form a semihydrated $TiO_2$ colloidal precipitate. As another example, the hydrogel is prepared by hydrolyzing titanium compounds at a pH of from about 2 to about 14 and then aging the hydrolysis product at a temperature from about 0° C. to about 200° C. or more, perferably in a closed container for a suitable time to provide the desired anatase/amorphous $TiO_2$ hydrogel. While the applicant does not wish to be bound by the prevailing theory or mechanism, it is thought that the hydrogel is formed as semihydrated $TiO_2$ comprising one or more anatase form crystalline domains within amorphous $TiO_2$ therein. Although the hydrogel is primarily anatase/amorphous $TiO_2$, the hydrogel may also contain other materials, for example, materials present in the starting materials or formed incident to the hydrolysis reaction, including counterions. Typically the hydrogel has one or more anatase form crystalline domains having a crystalline dimension of from about 3 nm to 10 nm, preferably about 5 nm. The hydrogel can be aged or ripened for various periods to facilitate crystallization to the desired crystalline dimension, but this step is not always necessary. As used herein, the term "crystalline dimension" refers to the size and "crystalline domain" refers to the place of the anatase crystal in the hydrogel.

In a preferred method the hydrogel is prepared by hydrolyzing titanium compounds in an aqueous or non-aqueous liquid medium at a pH of from about 2 to about 14 and then aging the hydrolysis product by heating the product to a temperature of from about 0° C. to about 200° C. or more for a period of time suitable to provide the desired anatase/amorphous $TiO_2$ hydrogel.

The titanium compound is preferably selected from titanium alkoxides, titanium halides, and the like, more preferably titanium ethoxide, titanium isopropoxide, $Ti(SO_4)_2$ or titanium chloride ($TiCl_4$), most preferably $TiCl_4$, or $Ti(SO_4)_2$. These materials are well known in the art. The aqueous medium or non-aqueous liquid medium may comprise water, and an acid or base as appropriate to cause the hydrolysis reaction, preferably a base is used. The preferred pH is from about 8 to about 14. The hydrolysis is preferably performed in the presence of a base, typically an inorganic base such as NaOH, $HH_4OH$ and the like, most preferably $NH_4OH$. Aging of the hydrolysis product is preferably caused by heating the product to a temperature of from about 150° C. to about 200° C., for a period of from about 6 to about 72 hours, preferably about 6-48 hours, more preferably about 6 to about 24 hours, preferably in a closed container, to provide the desired anatase/amorphous $TiO_2$ hydrogel. The hydrogel thus formed is less photoreactive than prior art anatase compositions.

The hydrogel can be used directly in the composition of the invention, or can be dried and particulated, powderized, ground or the like to form particles of anatase/amorphous $TiO_2$. The particles are more readily stored than the hydrogel, and can be used in the composition directly or after storage. The particles of the anatase/amorphous $TiO_2$ can also be described as a "powder" or "powder composition" which comprises anatase/amorphous $TiO_2$ particles ranging from about 50 to about 150 nm in size, preferably larger than about 50 nm to about 150 nm, more preferably from about 60 nm to about 150 nm in size, most preferably from about 60 nm to about 70 nm in size.

The particles are formed by powderizing methods which control particle size to within the 50 to 150 nm range. Several powderizing methods are known in the art, which methods may comprise heating milling, drying, and/or spraying the hydrogel and the like. For example, the particles may be formed by aging and then removing supernatant or water. Alternatively, the particles are prepared by powderizing and then heat treating, for example, to a temperature of from about 200° C. to about 800° C. for a period of about 1 to about 12 hours as appropriate. The resulting particles are typically low in water content, preferably less than 1% water, most preferably free from water.

The particles contain from about 20% to about 90% anatase crystal, preferably from about 20% to about 80% anatase, with the balance of the particle being substantially amorphous. Although the particles are primarily anatase/amorphous $TiO_2$, they may also contain other materials, for example, materials present in the starting materials for forming the hydrogel or formed incident to the hydrolysis reaction. Such other materials may include counterions incident to the process of preparing the $TiO_2$.

Whereas "crystalline domain size" is used in reference to the anatase/amorphous $TiO_2$ hydrogel, the term "particle size" is used in reference to the particles of the anatase/amorphous $TiO_2$. Particle size is determined by art recognized methods, such as by transmission electron microscopy, light scattering, gel filtration, gas absorption and the like. In using the term "particle size" when describing the $TiO_2$ particles and the term "crystalline domain size" when describing the crystals in the hydrogel, the term "size" is defined as an average because 1) the particles have a size range (i.e., they are not monodisperse); and 2) the dimensions of the particles may be irregular (i.e., they may not be entirely spherical, cubic or the like).

The anatase/amorphous $TiO_2$ hydrogel and the particles therefrom are useful in topical compositions including sunscreens, and are particularly adapted for use in topical sunscreen compositions. The topical compositions will typically comprise from about 1% to about 15% of the hydrogel, the particles or a combination thereof preferably about 3% to about 12% more preferably about 10%.

The anatase/amorphous $TiO_2$ particles having the indicated sizes and crystallinities provide $TiO_2$ sunscreens that are more effective than sunscreens containing $TiO_2$ known heretofore. While the applicant does not intend to be bound by theory, it is thought that the preferred range of crystallinity and particle size of the particles of this invention avoids the dulling and discoloration of the skin, allowing for a more transparent sunscreen.

In a preferred embodiment, the hydrogel of from about 20 to about 60% anatase/amorphous $TiO_2$ by weight is used for preparing a topical composition. Using this hydrogel to prepare the composition allows for ease in processing, more even coverage of the composition on a substrate (e.g., skin), further enhanced stability against photodegredation and degradation by air compared to the prior art anatase compositions, and other benefits. In particular, sunscreens comprising the hydrogel are found to be surprisingly stable. While the applicant does not intend to be bound by theory, it is thought that counterions remaining in the hydrogel may stabilize the hydrogel against photoreaction. Whatever the mechanism, the hydrogel avoids the photoreactivity generally associated with anatase $TiO_2$. Hence it can be formulated with organic actives, additives or the like, without fear of by-products forming or inactivation of the organic actives or additives as a result of the $TiO_2$ decomposition. As such, it provides a very stable sunscreen that does not lose its protecting power on extended exposure to UV light.

The hydrogel and/or particles are incorporated into the topical composition by standard mixing techniques as described herein below. The topical compositions useful in this invention may be formulated into a wide variety of product types. These include, but are not limited to solutions, lotions, creams, pastes, mousses, oils or ointments, gels, sticks, sprays, skin cosmetics and the like. These product types may be formulated using any of several types of carrier systems including, but not limited to solutions, suspensions, gels, emulsions, and the like. Preferred embodiments include gels or emulsions, more preferably emulsions.

The topical compositions comprise a cosmetically and pharmaceutically-acceptable carrier system for the anatase/amorphous $TiO_2$ and optionally other active materials that may be included in the composition (hereinafter alternatively referred to as "carrier system" or "carrier"). As used herein, "cosmetically and pharmaceutically acceptable" solvent or other material means that the material possesses acceptable safety properties (e.g., skin irritation and sensitization characteristics). The solvent or solvent mixture is capable of having dispersed therein the anatase/amorphous $TiO_2$ and optionally other active materials that may be included in the composition. The carrier system typically includes a cosmetically and pharmaceutically acceptable solvent (hereinafter "solvent"). The solvent typically comprises one or more aqueous or organic solvents, oils or a mixture thereof. Examples of suitable solvents include: propylene glycol, polyethylene glycol, polypropylene glycol, polyvinyl pyrrolidine, propylene glycol butyl ether, glycerol, 1,2,4-butanetriol, sorbitol esters, 1,2,6-hexanetriol, ethanol, isopropanol, butanediol, and the like and mixtures thereof. These and other solvents suitable for use in the invention are described in the C.T.F.A. Cosmetic Ingredient Handbook, 3rd Ed., Cosmetic and Fragrance Assn., Inc., Washington D.C. (1982), incorporated herein by reference.

Topical compositions in the form of a solution comprise a carrier system and may also comprise an emollient. Emollients are generally useful for the prevention or relief of skin dryness, as well as for the protection of the skin. A wide variety of suitable emollients are known and may be used herein. Sagarin, *Cosmetics, Science and Technology*, 2nd Edition, Vol. 1, pp. 32–43 (1972), incorporated herein by reference, contains numerous examples of suitable emollients.

Lotions, creams, oils and ointments may comprise any of the components described for solutions of the present invention and are usually differentiated therefrom by their higher viscosity (creams having a higher viscosity than lotions). Thus, the carrier system of such topical compositions may be in the form of a solution.

The lotions typically comprise from about 1% to about 20%, preferably from about 5% to about 10%, of an emollient; from about 50% to about 90%, preferably from about 60% to about 80%, water, and from about 1% to about 15% of the anatase/amorphous $TiO_2$ hydrogel solids, particles or a combination thereof, preferably about 3% by weight to about 12% by weight, more preferably about 10% based on the weight of the lotion.

A cream typically comprises from about 0.01% to about 20%, preferably from about 5% to about 50%, more preferably from about 10% to about 20%, of an emollient, from about 45% to about 85%, preferably from about 50% to about 75%, water, and from about 1% to about 15% of the anatase/amorphous $TiO_2$ hydrogel solids, particles or a combination thereof, about 3% by weight to about 12% by weight, more preferably about 10% based on the weight of the cream.

Oils and ointments are yet another type of topical composition of the present invention. The carrier system for oils and ointments may comprise a simple base of animal or vegetable oils or hydrocarbons. Ointments may also comprise as a carrier system an absorption ointment base which absorbs water to form emulsions. The carrier system may alternatively be water soluble. An ointment may also comprise from about 2% to about 10% of an emollient plus from about 0.1% to about 2% of a thickening agent, based on the weight of the ointment. A more complete disclosure of thickening agents useful herein can be found in Segarin, *Cosmetics, Science and Technology*, 2nd Edition, Vol. 1, pp. 72–73 (1972). The oil or ointment typically comprises from about 1% to about 15% of the anatase/amorphous $TiO_2$ hydrogel solids, particles or a combination thereof, about 3% by weight to about 12% by weight, more preferably about 10% based on the weight of the composition.

Suspensions are a form of carrier system of the topical compositions of the invention. The suspension typically comprises one or more suspending agents. Such agents are known and used in the art.

A preferred embodiment of the invention is formulated as an emulsion. If the carrier system is formulated as an emulsion, preferably from about 1% to about 10%, more preferably from about 2% to about 5%, of the carrier system comprises an emulsifier. Emulsifiers may be nonionic, anionic or cationic. Suitable emulsifiers are disclosed in, for example, U.S. Pat. No. 3,755,560, issued Aug. 28, 1973, Dicker et at, U.S. Pat. No. 4,421,769, issued Dec. 20, 1983, Dixon et al.; and McCutcheon's *Detergents and Emulsifiers*, North American Edition, pages 317–324 (1986); the disclosures of which are incorporated herein by reference. Preferred emulsifiers are anionic or nonionic, although the other types may also be used.

Lotions, creams, pastes and mousses can be formulated as emulsions as well as solutions. Single emulsion skin care preparations, such as lotions and creams, of the off-in-water type and water-in-off type are well known in the cosmetic art and are useful in this invention. Such emulsions can stabilize the actives. Multiphase emulsion compositions, such as the water-in-oil-in-water type, as disclosed in U.S. Pat. No. 4,254,105, Fakuda et al., issued Mar. 3, 1981, incorporated herein by reference, are also useful in this invention. In general, such single or multiphase emulsions contain water, emollients and emulsifiers as essential ingredients. Triple emulsion carrier systems comprising an oil-in-water-in-silicone fluid emulsion composition as disclosed in U.S. Pat. No. 4,960,764, Figueroa, issued Oct. 2, 1990, are also useful in this invention. Judicious choice of surfactant for promotion of stability and penetration will enhance the beneficial properties of the invention.

Liposomal formulations, which are related to emulsions, are also useful as topical compositions of this invention. Such compositions can be prepared by first combining the $TiO_2$ active with a phospholipid, such as dipalmitoylphosphatidyl choline, cholesterol and water according to the method described in Mezei & Gulasekharam, "Liposomes—A Selective Drug Delivery System for the Topical Route of Administration: Gel Dosage Form", *Journal of Pharmaceutics and Pharmacology*, Vol. 34 (1982), pp. 473–474, incorporated herein by reference, or a modification thereof. Epidermal lipids of suitable composition for forming liposomes may be substituted for the phospholipid. The liposome preparation is then incorporated into one of the carrier systems (for example, a gel or an oil-in-water emulsion) in order to produce the liposomal formulation. Other compositions and pharmaceutical uses of topically applied liposomes are described in Mezei, M., "Liposomes as a Skin Drug Delivery System", *Topics in Pharmaceutical Sciences* (D. D. Breimer and P. Speiser, eds.), Elsevier Science Publishers B. V., New York, N.Y., 1985, pp. 345–358, incorporated herein by reference.

If the topical compositions useful in this invention are formulated as a gel (including a cosmetic stick), such compositions can be formulated by the addition of a suitable amount of a thickening agent, for example, to a cream or lotion formulation. Topical compositions useful in this invention may also be formulated as makeup products.

The topical compositions useful in this invention can be formulated as an aerosol and applied to the skin as a spray-on. To form an aerosol, a propellant is added to a solution or emulsion composition. Examples of propellants useful herein include, but are not limited to, hydrocarbons and the chlorinated, fluorinated and chloro-fluorinated lower molecular weight hydrocarbons and the like. A more complete disclosure of propellants can be found in Sagarin, *Cosmetics Science and Technology*, 2nd Edition, Vol. 2, pp. 443–465 (1972).

Of course, any of the compositions of the invention can also optionally contain other cosmetically and pharmaceutically acceptable ingredients, including, but not limited to those discussed below.

a. Colorants and finishing agents

Colorants are present in a concentration sufficient to provide a pleasing color to the topical composition when applied and in the container in which the composition is sold. Colorants may also provide additional sunscreen activity. There are no specific limitations as to the pigment, colorant, dye or finishing agent powders used in the composition. They may be inorganic pigments, pearling agents, and the like. Specific examples are talc, mica, magnesium carbonate, calcium carbonate, magnesium silicate, aluminum magnesium silicate, silica, zinc oxide, red iron oxide, yellow iron oxide, black iron oxide, nylon powder, polyethylene powder, methacrylate powder, polystyrene powder, silk powder, crystalline cellulose, starch, titanated mica, iron oxide titanated mica, bismuth oxychloride, and the like. These colorants and powders can be used independently or in combination. Determination of the desired levels and/or choice of colorants is within the skill of the artisan. Preferred colorants that are generally recognized as safe, and are listed in C.T.F.A. Cosmetic Ingredient Handbook, 3rd Ed., Cosmetic and Fragrance Assn., Inc., Washington, D.C. (1982), incorporated herein by reference, are used.

b. Waxes

Waxes can provide a "good skin feel," and pleasant application characteristics to the composition. Waxes are lower-melting organic mixtures or compounds of high molecular weight, solid at room temperature and generally similar in composition to fats and oils except that they contain no glycerides. They can be hydrocarbons, esters of fatty acids or alcohols. Waxes useful in the present invention are selected from the group consisting of animal waxes, vegetable waxes, mineral waxes, natural waxes, synthetic waxes, petroleum waxes, ethylenic polymers, hydrocarbons, silicone waxes, and mixtures thereof.

c. Moisturizers

Optionally, one or more moisturizing agents can be used in the composition. Among the moisturizing agents useful in the composition are such well known cosmetically effective moisturizing agents as glycerin, hydrogen starch hydrolysate, sorbitol, glycerol monopropoxylate, hydrolyzed silk and the like. Many of these agents are defined in the C.T.F.A. Cosmetic Ingredient Handbook, 3rd Ed., Cosmetic and Fragrance Assn., Inc., Washington D.C. (1982), incorporated herein by reference.

d. Fragrances

In addition, a fragrance is optionally present in the above composition in a concentration to provide a pleasant scent during application.

e. Preservatives

Typically preservatives, including those listed in C.T.F.A. Cosmetic Ingredient Handbook, 3rd Ed., Cosmetic and Fragrance Assn., Inc., Washington D.C. (1982) pp. 575–580, incorporated herein by reference, are used. The levels of these preservatives are readily determined by those skilled in the art. For example, favored levels are often less than 5% and typically less than 1%, based on the weight of the composition.

f. Stabilizers

Other material can be incorporated to provide added stability at storage temperature and the like.

g. Clays

Water dispersible and oil dispersible clays may also be useful to thicken the invention. Certain clays, such as kaolin, may also provide additional suncreening. The water dispersible clays comprise bentonite and hectorite, such as Bentone E W, L T from Rheox; magnesium aluminum silicate, such as Veegum from Vanderbilt Co.; attapulgite such as Attasorb or Pharmasorb from Engelhard, Inc.; laponite and montmorrilonite, such as Gelwhite from ECC America; and mixtures thereof. The oil dispersible days comprise quaternium-18 bentonite, such as Bentone 34 and 38 from Rheox; the Claytone Series from ECC America; quaternium-18 hectorite, such as Bentone gels from Rheox; and mixtures thereof.

h. Combination actives

1. Organic Sunscreens

A wide variety of conventional organic sunscreening agents are suitable for use in combination with the sunscreen agent. Segarin, et at., at Chapter VIII, pages 189 et seq., of *Cosmetics Science and Technology*, disclose numerous suitable agents. Specific suitable sunscreening agents include, for example: p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, benzyl, menthyl, glyceryl, and dipropyleneglycol esters); cinnamic acid derivatives (menthyl and benzyl esters, cc-phenyl cinnamonitrile; butyl cinnamoyl pyruvate); dihydroxycinnamic acid derivatives (umbelliferone, methylumbelliferone, methylacetoumbelliferone); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); dihydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and vilouric acids; tannic acid and its derivatives (e.g., hexaethylether); (butyl carbotol) (6-propyl piperonyl) ether; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; 4,4'-t-butylmethoxydibenzoylmethane; and etocrylene); camphor derivatives, 3,3'-(1,4-phenylenedimethylidene) bis(7,7-dimethyl-2-oxo-bicyclo[2.2.1]heptane-1-methanesulfonic acid)sodium salt and the like.\*\*\*BOOK\*\*\*

Of these, 2-ethylhexyl-p-methoxycinnamate, 4,4'-t-butylmethoxydibenzoyl-methane, 2-hydroxy-4-methoxybenzophenone, octyldimethyl-p-aminobenzoic acid, digalloyl-trioleate, 2,2-dihydroxy-4-methoxybenzophenone, ethyl-4-(bis(hydroxypropyl)) aminobenzoate, 2-ethylhexyl-2-cyano-3,3-diphenylacrylate, 2-ethylhexylsalicylate, glyceryl-p-aminobenzoate, 3,3,5-trimethylcyclohexylsalicylate, methylanthranilate, p-dimethyl-aminobenzoic acid or aminobenzoate, 2-ethylhexyl-p-dimethyl-amino-benzoate, 2-phenylbenzimidazole-5 -sulfonic acid, 2-(p-dimethylamino-phenyl)-5-sulfonicbenzoxazoic acid and mixtures of these compounds, are preferred.

More preferred sunscreens useful in the compositions useful in this invention are 2-ethylhexyl-p-methoxycinnamate, 4,4'-t-butylmethoxydibenzoylmethane, 2-hydroxy-4-methoxybenzophenone, octyldimethyl-p-aminobenzoic acid and mixtures thereof.

Also particularly useful in the compositions are sunscreens such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991, both of which are incorporated herein by reference. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methylaminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl) methylaminobenzoic acid ester with 4-hydroxydibenzoylmethane; 4-N,N-(2-ethylhexyl) methylaminobenzoic acid ester of 2-hydroxy-4-(2-hydroxyethoxy)benzophenone; 4-N,N-(2-ethylhexyl)-methylaminobenzoic acid ester of 4-(2-hydroxyethoxy) dibenzoylmethane; N,N-di-(2-ethylhexyl)4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy)dibenzoylmethane and mixtures thereof.

The composition preferably comprises up to about 20%, preferably up to about 10%, of an organic sunscreening agent, based on the weight of the composition. Exact amounts will vary depending upon the sunscreen chosen and the desired Sun Protection Factor (SPF).

An agent may also be added to any of the compositions useful in this invention to improve the skin substantivity of those compositions, particularly to enhance their resistance to being washed off by water, or rubbed off. Such agents are often polymers and preferably film-forming polymers. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

2. Anti-Inflammatory Agents

Optionally, an anti-inflammatory agent is included. In addition to the known anti-inflammatory advantages imparted, often the anti-inflammatory agent protects against UVA radiation (and may provide some UVB protection as well). The topical use of anti-inflammatory agents also reduces darkening of the skin resulting from chronic exposure to UV radiation. (See U.S. Pat. No. 4,847,071, Bissett, Bush, and Chatterjee, issued Jul. 11, 1989, incorporated herein by reference; and U.S. Pat. No. 4,847,069, Bissett and Chatterjee, issued Jul. 11, 1989, incorporated herein by reference.)

A safe and effective amount of an anti-inflammatory agent may be added to the compositions useful in this invention, preferably from up to about 10%, more preferably from about 0.5% to about 5%, based on the weight of the composition. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, fluocinonide, fludrocortisone, difluorosone diacetate, fluadrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

A second class of anti-inflammatory agents which is useful in the compositions includes the non-steroidal anti-inflammatory agents. The variety of compounds encompassed by this group are well-known to those skilled in the art. For detailed disclosure of the chemical structure, synthesis, side effects, etc., of non-steroidal anti-inflammatory agents, reference may be had to standard texts, including *Anti inflammatory and Anti-Rheumatic Drugs*, K. D. Rainsford, Vol. I–III, CRC Press, Boca Raton, (1985), and *Anti-inflammatory Agents, Chemistry and Pharmacology*, 1, R. A. Scherrer, et at., Academic Press, New York (1974).

Specific non-steroidal anti-inflammatory agents useful in the composition invention include, but are not limited to:

1) the oxicams, such as piroxicam, isoxicam, tenoxicam, sudoxicam, and CP-14,304;

2) the salicylates, such as aspirin, disalcid, benorylate, trilisate, safapryn, solprin, diflunisal, and fendosal;

3) the acetic acid derivatives, such as diclofenac, fenclofenac, indomethacin, sulindac, tolmetin, isoxepac, furofenac, tiopinac, zitometacin, acematacin, fentiazac, zomepiract, clidanac, oxepinac, and felbinac;

4) the fenamates, such as mefenamic, meclofenamic, flufenamic, niflumic, and tolfenamic acids;

5) the propionic acid derivatives, such as ibuprofen, naproxen, benoxaprofen, flurbiprofen, ketoprofen, fenoprofen, fenbufen, indoprofen, pirprofen, carprofin, oxaprozin, pranoprofen, miroprofen, tioxaprofen, suprofen, alminoprofen, and tiaprofenic; and 6) the pyrazoles, such as phenybutazone, oxyphenbutazone, feprazone, azapropazone, and trimethazone.

Mixtures of these non-steroidal anti-inflammatory agents may also be employed, as well as the pharmaceutically-acceptable salts and esters of these agents. For example, etofenamate, a flufenamic acid derivative, is particularly useful for topical application. Of the non-steroidal anti-inflammatory agents, ibuprofen, naproxen, flufenamic acid, mefenamic acid, meclofenamic acid, piroxicam and felbinac are preferred; ibuprofen, naproxen, and flufenamic acid are most preferred.

Another class of anti-inflammatory agents which are useful in the compositions are the anti-inflammatory agents disclosed in U.S. Pat. No. 4,708,966, Loomans et at., issued Nov. 24, 1987. This patent discloses a class of non-steroidal anti-inflammatory compounds which comprise specifically substituted phenyl compounds, especially substituted 2,6-di-tert-butyl phenol derivatives. For example, compounds selected from 4-(4'-pentyn-3'-one)-2,6-di-t-butylphenol; 4-(5'-hexynoyl)-2,6-di-t-butylphenol; 4-((S)-(−)-3'-methyl-5'-hexynoyl)-2,6-di-t-butylphenol; 4-((R)-(+)-3'-methyl-5'-hexynoyl)-2,6-di-t-butylphenol; and 4-(3',3'-dimethoxypropionyl)-2,6-di-t-butylphenol are useful in methods of this invention; 4-(5'-hexynoyl)-2,6-d-t-butylphenol is most preferred.

Yet another class of anti-inflammatory agents which are useful in the compositions are those disclosed in U.S. Pat. No. 4,912,248, Mueller, issued Mar. 27, 1990. This patent discloses compounds and diastereomeric mixtures of specific 2-naphthyl- containing ester compounds, especially naproxen ester and naproxol ester compounds, having two or more chiral centers. For example, compounds selected from (S)-naproxen-(S)-2-butyl ester, (S)-naproxen-(R)-2-butylester, (S)-naproxol-(R)-2-methyl butyrate, (S)-naproxol-(S)-2-methyl butyrate, diasteromeric mixtures of (S)-naproxen-(S)-2-butyl ester and (S)-naproxen- (R)-2-butyl ester, and diasteromeric mixtures of (S)-naproxol-(R)-2-methyl butyrate and (S)-naproxol-(S)-2-methyl butyrate are useful in this invention.

Finally, so-called "natural" anti-inflammatory agents are useful in methods of this invention. For example, candelilla wax, alpha bisabolol, aloe vera, Manjistha (extracted from plants in the genus Rubin, particularly Rubia Cordifolia), and Guggal (extracted from plants in the genus Commiphora, particularly Commiphora Mukul), may be used.

3. Anti-Oxidants/Radical Scavengers

Optionally, an anti-oxidant/radical scavenger is included. A safe and effective amount of an anti-oxidant/radical scavenger may be added to the compositions useful in this invention, when used, they are preferably from about 0.1% to about 10%, more preferably from about 1% to about 5%, based on the weight of the composition.

Anti-oxidants/radical scavengers such as ascorbic acid (vitamin C) and its salts, tocopherol (vitamin E), tocopherol sorbate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, the ascorbyl esters of fatty acids, amines (e.g., N,N-diethylhydroxylamine, aminoguanidine), sulfhydryl compounds (e.g., glutathione), and dihydroxy fumaric acid and its salts may be used.

4. Chelators

Optionally, a chelating agent is included along with the anatase/amorphous $TiO_2$. As used herein, "chelating agent" means an active agent capable of removing a metal ion from a system by forming a complex so that the metal ion cannot readily participate in or catalyze chemical reactions.

A safe and effective amount of a chelating agent may be added to the compositions useful in this invention, preferably from about 0.1% to about 10%, more preferably from about 1% to about 5%, based on the weight of the composition. Chelators useful in compositions are disclosed in U.S. patent application Ser. No. 619,805, Bissett, Bush & Chatterice, filed Nov. 27, 1990 (which is a continuation of U.S. patent application Ser. No. 251,910, filed Oct. 4, 1988); U.S. patent application Ser. No. 514,892, Bush & Bissett, filed Apr. 26, 1990; and U.S. patent application Ser. No. 657,847, Bush, Bissett & Chatterjee, filed Feb. 25, 1991; all incorporated herein by reference. Preferred chelators useful in compositions of this invention are furildioxime and derivatives thereof.

5. Retinoids

Optionally, a retinoid, preferably retinoic acid, is included along with the anatase/amorphous $TiO_2$. A safe and effective amount of a retinoid may be added to the compositions useful in this invention, preferably from about 0.001% to about 2%, more preferably from about 0.01% to about 1%, based on the weight of the composition. As used herein, "retinoid" includes all natural and/or synthetic analogs of Vitamin A (retinol) or retinol-like compounds which possess the biological activity of Vitamin A in the skin as well as the geometric isomers and stereo isomers of these compounds, such as all-trans retinoic acid and 13-cis-retinoic acid.

Compositions may comprise any or a mixture of additional actives along with the anatase/amorphous $TiO_2$. This invention may also include humectants, proteins and polypeptides, preservatives, buffering agents (as that described in copending U.S. patent application Ser. No. 08/334,466 incorporated herein by reference) and neutralizing agent(s). In addition, the topical compositions useful herein can contain conventional cosmetic adjuvants, such as dyes and colorants, opacifiers, pigments, including inorganic pigments and the like, such as zinc oxide, iron oxide, rutile $TiO_2$, etc., which may add additional sunscreening.

Other skin care product additives may also be included in the compositions useful in this invention. For example, collagen, hyaluronic acid, elastin, hydrolysates, primrose oil, jojoba oil, epidermal growth factor, soybean saponins, benzoyl peroxide, mucopolysaccharides, and mixtures thereof may be used. Also desquamation agents and exfoliating agents, including alpha-hydroxy acids, such as glycolic acid, lactic acid, and the like, salicylic acid, zwitterionic surfactants, such as cetyl betaine and the like may be added.

Various vitamins may also be included in the compositions useful in this invention. For example, Vitamin A, and derivatives thereof, Vitamin $B_2$, biotin, pantothenic acid, Vitamin D, and mixtures thereof may be used.

Compositions thus prepared are useful as sunscreens. They are applied to the skin in a manner similar to conventional sunscreens and provide protection against UVA/UVB radiation. Application of the composition to the skin can take place before or during exposure to sun.

EXAMPLES

The following examples are provided to illustrate embodiments of the invention. The examples do not limit the invention in any way, but rather are presented to instruct the artisan specifically how to make and use the invention.

The following non-limiting examples are provided to illustrate the preparation of anatase/amorphous $TiO_2$ and topical compositions containing the same in accordance with the present invention.

Preparation of an anatase/amorphous $TiO_2$

The following non-limiting examples illustrate laboratory preparation of the anatase/amorphous $TiO_2$.

Example 1

Hydrogel:

Dissolve $TiCl_4$ (Aldrich) in ethanol, then titrate it with a solution of $NH_4OH$ to about pH 2. Once mixed, age (i.e., ripen) the solution in a closed system at about 150° C. for about 24 hours. Adjust the solution to about pH 6 with $NH_4OH$. Centrifuge the flocculated material, decant the supernatant and rinse the resultant hydrogel with distilled water.

Particles:

Wash the hydrogel above with ethanol, and heat it with trituration. Powderize the dried material with a grinding to the desired particle size. The particle size can be determined with transmission electron microscopy (TEM).

Example 2

Mix 16.8 ml of $TiCl_4$ (99.9%-Aldrich) with 33.2 ml of ethanol. Add this $TiCl_4$/ethanol solution to a 350 mi of 3.2M $NH_4OH$ solution by titrating. A hydrogel forms.

Heat the hydrogel to 150° C. for 24 hours. After 24 hours wash the resultant hydrogel with water to a neutral pH or adjust to pH 5–6. Wash and filter the gel. The gel can then be powderized to form particles as described above.

The particles or the hydrogel can be incorporated into a topical composition which is suitable, for example, as a sunscreen.

Formulation Examples

The following non-limiting examples illustrate the preparation of topical compositions according to the present invention.

Example 3

Particles of the appropriate size (based on TEM measurements) are incorporated into a standard sunscreen formulation:

|  | % w/w |
|---|---|
| Phase A | |
| Cetyl Dimethicone Copolyol and Polyglycerol-4 Isostearate and Hexyl Laurate (1) | 5.0 |
| Mineral oil | 5.0 |
| Octyl Stearate | 6.0 |
| Cyclomethicone (2) | 4.0 |
| Cetyl Dimethicone (3) | 1.0 |
| Isopropyl Myristate | 4.0 |
| Hydrogenated castor oil | 0.8 |
| Microcrystalline wax | 1.2 |
| Phase B | |
| Water | 62.2 |
| $TiO_2$ particles | 10.0 |
| Sodium Chloride | 0.8 |
| Total | 100.0 |

(1) Abil WE-09
(2) Abil B 8839
(3) Abil wax 9801

Heat Phase A and stir to dissolve waxes. Dissolve salt in water, to this mixture add $TiO_2$ and disperse. Combine phases while homogenizing.

Formulation Example 4

When the $TiO_2$ hydrogel is used in the place of dry particles, one simply alters the amount of water added in accordance with the $TiO_2$ solids of the hydrogel in the formulation. Hydrolyze $TiCl_4$ (Aldrich) in $NH_4OH$, ripen and neutralize. The formulation prepared below is comparable to that of example I in terms of formulation, but uses the hydrogel in place of the $TiO_2$ particles, by decreasing the amount of water used in the formula:

| Phase A | % w/w |
|---|---|
| Cetyl Dimethicone Copolyol and Polyglycerol-4 Isostearate and Hexyl Laurate (1) | 5.0 |
| Mineral oil | 5.0 |

Make the sunscreen in a manner analogous to the first example.

Immediate Pigment Darkening (IPD) Measurement

This photoprotection test was done according to the method published by Kaidbey, K. H. and Barnes, A., "Determination of UVA protection factors by means of immediate pigment darkening in normal skin", *J. Am. Acad. Dermatol.*, 25:262–6, 1991.

The invention's sunscreen formulations do not darken (or photoreact) upon standing (e.g., about 15 minutes) in sunlight. The invention has unexpected photostability. While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A topical composition comprising:
   a) as an active from about 1% to about 15% anatase crystal in amorphous $TiO_2$ chosen from the group consisting of;
      1) a hydrogel comprising about 20% to about 60% solids comprising about 20% to about 90% anatase crystal in amorphous $TiO_2$ having average crystalline domain dimensions of about 3 nm to about 10 nm; and
      2) a $TiO_2$ particle comprising about 20% to about 90% anatase form wherein the particles are from about 50 nm to about 150 nm in size; and
   b) a cosmetically acceptable topical carrier.

2. A composition according to claim 1 wherein the composition is a sunscreen.

3. A topical composition according to claim 1 wherein the anatase crystal in amorphous $TiO_2$ is incorporated as a hydrogel.

4. A topical composition according to claim 1 wherein the hydrogel has average crystalline dimensions of about 5 nm.

5. A topical composition according to claim 1 comprising as an active from about 1% to about 15% anatase crystal in amorphous $TiO_2$ particles from about 20% to about 90% anatase form, ranging in size from at least about 50 nm to about 150 nm in size.

6. A topical composition according to claim 5 wherein the particles are from about 20% to about 80% anatase form.

7. A topical composition according to claim 5 wherein the particles range in size from at least about 60 nm to about 70 nm in size.

8. A topical composition according to claim 7 wherein the particles are from about 20% to about 80% anatase form, ranging in size from about 60 nm to about 70 nm in size.

9. A topical composition according to claim 1 wherein the composition is a non-discoloring sunscreen.

10. A topical composition according to claim 1 wherein the composition is invisible upon application.

11. A topical composition according to claim 1 wherein the composition is a UVA and UVB shielding sunscreen.

12. A topical composition, useful as a sunscreen according to claim 1 wherein the composition is an emulsion chosen from the group consisting of a water-in-oil emulsion and an oil-in-water emulsion.

* * * * *

UNITED STATES PATENT AND TRADEMARK OFFICE
CERTIFICATE OF CORRECTION

PATENT NO. : 5,700,451

DATED : 12/23/97

INVENTOR(S) : Yue et al.

It is certified that error appears in the above-identified patent and that said Letters Patent is hereby corrected as shown below:

In Col. 1, line 27, "days" should read --clays--.

In Col. 2, line 9, "natural" should read --unnatural--.

In Col. 6, line 62, "Dicker" should read --Dickert--.

In Col. 6, line 62, "at," should read --al.,--.

In Col. 7, line 3, "off" should read --oil--.

In Col. 7, line 4, "off" should read --oil--.

In Col. 8, line 63, "days" should read --clays--.

In Col. 9, line 5, "at.," should read --al.,--.

In Col. 9, line 15, "cc-phenyl" should read --α-phenyl--.

In Col. 10, line 65, "fluocinonide" should read --flucetonide--.

In Col. 10, line 66, "fluadrenolone" should read --fluradrenolone--.

In Col. 11, line 20, "at.," should read --al.,--.

In Col. 11, line 30, "zitometacin" should read --zidometacin--.

In Col. 11, line 37, "carprofin" should read --carprofen--.

In Col. 11, line 54, "at.," should read --al.,--.

In Col. 12, line 16, "Rubin" should read --Rubia--.

In Col. 12, line 50, "Chatterice" should read --Chatterjee--.

In Col. 13, line 22, "betainc" should read --betaine--.

In Col. 13, line 62, "mi" should read --ml--.

UNITED STATES PATENT AND TRADEMARK OFFICE
CERTIFICATE OF CORRECTION

PATENT NO. : 5,700,451

DATED : 12/23/97

INVENTOR(S) : Yue et al.

It is certified that error appears in the above-identified patent and that said Letters Patent is hereby corrected as shown below:

In Col. 14, line 52, insert

| | |
|---|---|
| --Octyl Stearate | 6.0 |
| Cyclomethicone (2) | 4.0 |
| Cetyl Dimethicone (3) | 1.0 |
| Isopropyl Myristate | 4.0 |
| Hydrogenated castor oil | 0.8 |
| Microcrystalline wax | 1.2 |
| Phase B | |
| Water | 52.2 |
| $TiO_2$ (hydrogel at 50% solids) | 20.0 |
| Sodium Chloride | 0.8 |
| Total | 100.0 |

(1) Abil WE-09

(2) Abil B 8839

(3) Abil wax 9801--.

Signed and Sealed this

Fifteenth Day of February, 2000

*Attest:*

Q. TODD DICKINSON

*Attesting Officer*   Commissioner of Patents and Trademarks